United States Patent [19]
Fan

[11] Patent Number: 5,184,652
[45] Date of Patent: Feb. 9, 1993

[54] UNIVERSAL MEDICATION PORT

[76] Inventor: Chin-Fu Fan, 112 E. 83rd St., Apt. 6A, New York, N.Y. 10028

[21] Appl. No.: 724,756

[22] Filed: Jul. 2, 1991

[51] Int. Cl.$^5$ .................. A61M 39/00; F16K 3/00
[52] U.S. Cl. .................... 141/21; 141/346; 141/349; 141/387; 604/83; 604/249; 251/149.6
[58] Field of Search ............ 604/249, 246–248, 604/236, 207, 121, 82, 83, 85, 30, 32, 33; 251/149.6, 149.1, 149.7; 141/382, 383, 385, 349, 387–389, 346, 348, 18, 21, 25–28

[56] References Cited

U.S. PATENT DOCUMENTS

| 2,866,457 | 12/1956 | Moore | 604/83 |
|---|---|---|---|
| 3,276,472 | 12/1963 | Jinkens et al. | 137/556 |
| 3,561,433 | 2/1971 | Kovach | 604/249 X |
| 3,678,959 | 7/1972 | Liposky | 604/33 X |
| 3,994,293 | 11/1976 | Ferro | 604/83 |
| 4,029,125 | 6/1977 | Steydle et al. | 251/149.6 X |
| 4,036,210 | 7/1977 | Campbell et al. | 604/33 X |
| 4,193,406 | 3/1980 | Jinotti | 604/33 X |
| 4,335,717 | 6/1982 | Bujan et al. | 604/83 |
| 4,650,470 | 3/1987 | Epstein | 604/33 X |
| 4,666,429 | 5/1987 | Stone | 604/83 |
| 4,676,256 | 6/1987 | Golden | 604/249 X |
| 4,757,919 | 7/1988 | Smazik et al. | 251/149.6 X |
| 4,871,353 | 10/1989 | Thomsen | 604/83 |
| 4,915,687 | 4/1990 | Sivert | 604/83 |
| 4,957,483 | 9/1990 | Gonser et al. | 604/30 |
| 4,967,797 | 11/1990 | Manska | 137/625.47 |
| 5,097,842 | 3/1992 | Bonn | 604/33 X |

FOREIGN PATENT DOCUMENTS

| 0132870 | 4/1933 | Fed. Rep. of Germany | 604/248 |
|---|---|---|---|
| 0748666 | 7/1933 | France | 604/249 |
| 0294625 | 2/1971 | U.S.S.R. | 604/236 |

Primary Examiner—Henry J. Recla
Assistant Examiner—Casey Jacyna
Attorney, Agent, or Firm—Ostrolenk, Faber, Gerb & Soffen

[57] ABSTRACT

A universal medication port includes a cylindrical member having an internal bore with a plurality of radial passageways extending therefrom. A plunger is disposed within the internal bore of the cylinder, the plunger having an internal bore with a plurality of radial passageways extending therefrom. The plunger is movable in response to insertion of a needle-less hypodermic syringe into the internal bore of the cylindrical member so as to align the respective passageways in the plunger and the cylindrical member with one another to establish a fluid path from the syringe through the internal bore of the plunger and respective passageways in the plunger and the cylindrical member to a receptacle, such as a vial, an intravenous bottle or intravenous delivery system, in which the cylindrical member is inserted.

11 Claims, 2 Drawing Sheets

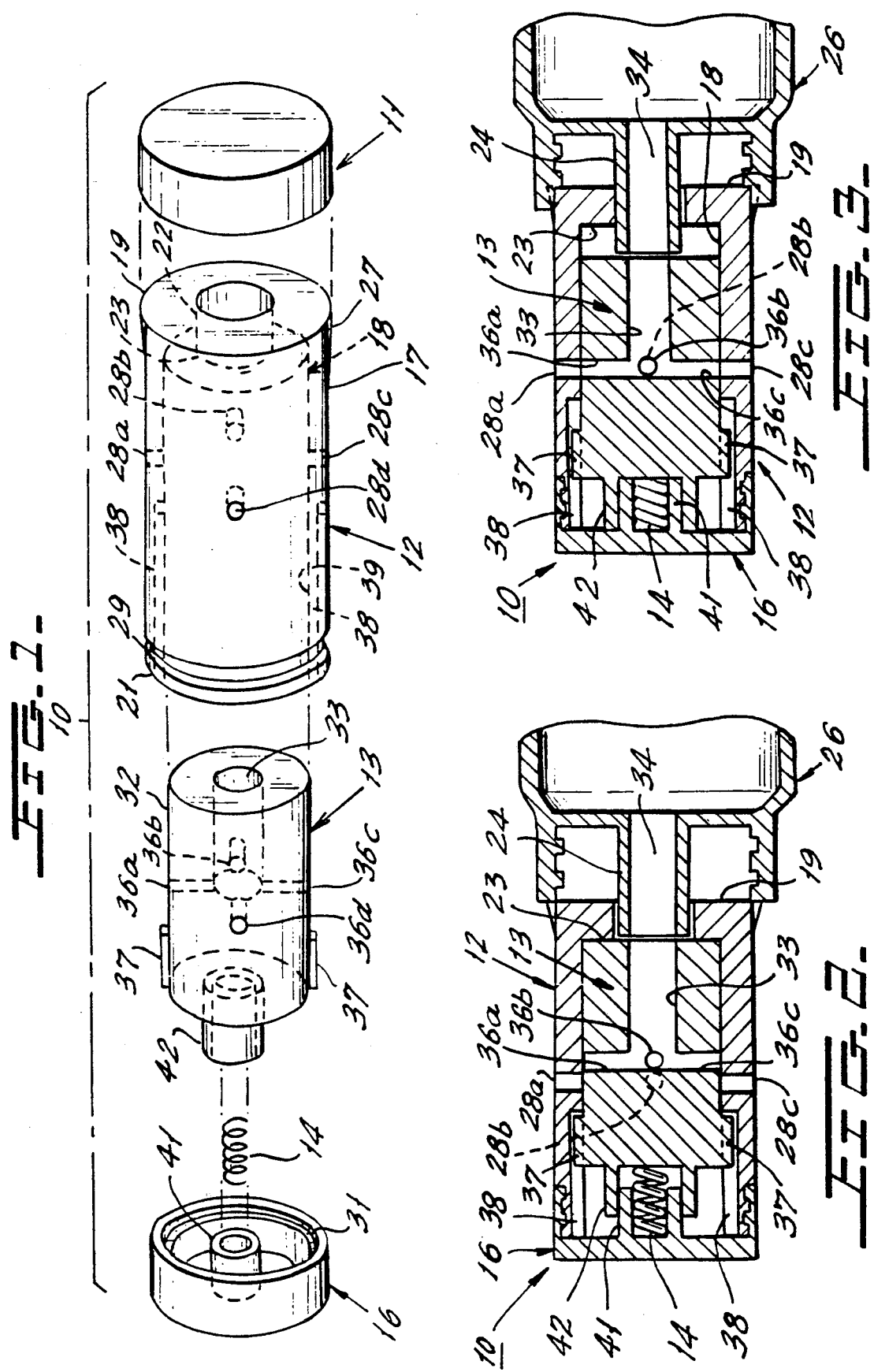

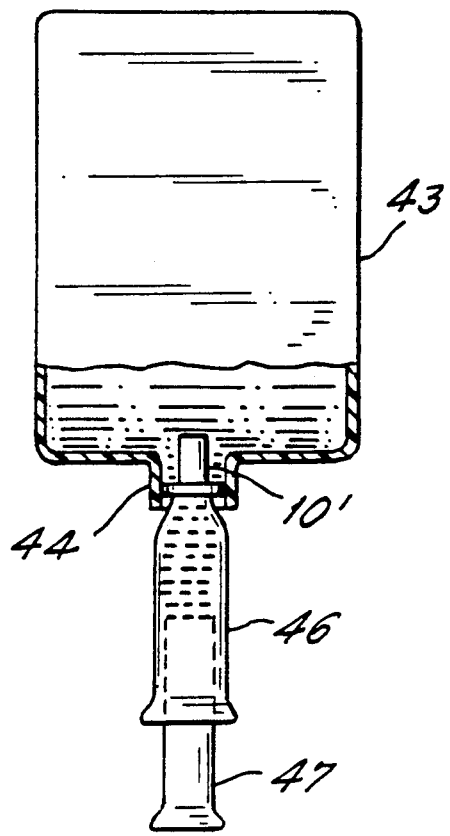
FIG. 4.
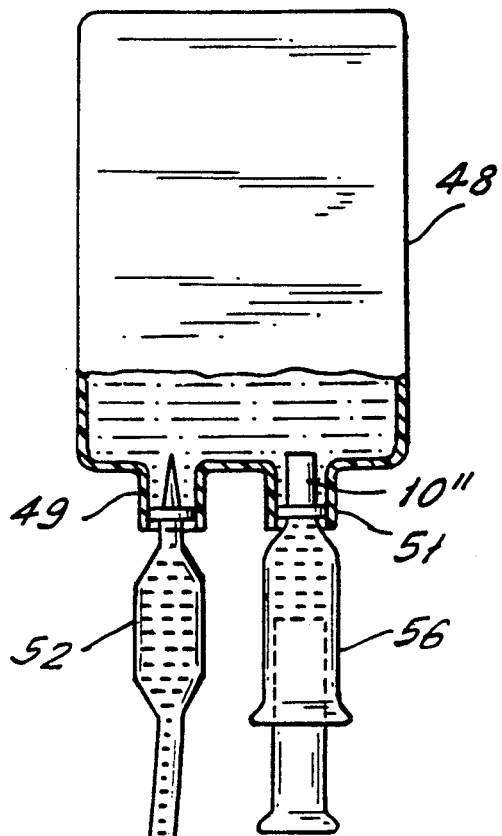
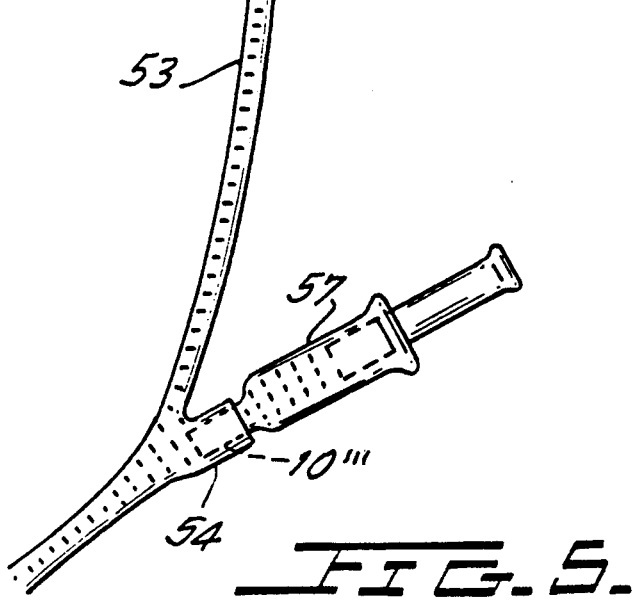
FIG. 5.

UNIVERSAL MEDICATION PORT

BACKGROUND OF THE INVENTION

The present invention relates to medication ports and, in particular, to a universal medication port that will enable any medicant or other type of fluid to be injected into or withdrawn from a vial, intravenous bottle, intravenous tubing or the like without the use of a hypodermic needle.

Intravenous delivery systems generally employ a length of tubing having means through which additional fluid or medication may be introduced. In the past, there have been a number of approaches for introducing additional fluid or medication to the intravenous tubing without using a hypodermic needle. Examples of such approaches can be found in U.S. Pat. Nos. 2,866,457; 3,276,472; 3,994,293; 4,666,429; 4,871,353; 4,915,687; and 4,967,797. All of these systems, however, are only suitable for introducing fluid into the delivery system itself. However, prior to the fluid or medication being introduced into the intravenous system, it must be withdrawn from a vial or intravenous bottle. This is generally accomplished in the prior art by using a hypodermic needle to withdraw medication or solution from the vial or intravenous bottle by aspiration. As a result, healthcare workers still run the risk of being accidently stuck by contaminated needles with the concomitant risk of infection.

SUMMARY OF THE INVENTION

Accordingly, it is an object of the present invention to provide a universal medication port which will enable medication or any other fluid to be withdrawn from a vial, intravenous bottle, intravenous tubing or the like, and to be injected into an intravenous delivery system without the use of a hypodermic needle, thereby eliminating the risk of healthcare workers being stuck by contaminated needles The foregoing and other objects are achieved in accordance with the present invention by a universal medication port which may be easily incorporated into a vial, intravenous bottle, intravenous tubing or the like so that intravenous fluid administration may be effected without the use of a hypodermic needle. Briefly, in accordance with the present invention, the universal medication port comprises a cylindrical member having an outer circumferential surface, first and second opposed ends, an internal bore extending axially within the cylindrical member from the first end to the second end, and at least one fluid passageway extending radially from the internal bore to the outer circumferential surface. A plunger is positioned within the internal bore of the cylindrical member such as to be actually movable therein. The plunger includes an outer circumferential surface, first and second opposed ends, an internal bore extending axially within the plunger from the first end toward the second end, and at least one passageway extending radially from the internal bore of the plunger to the outer circumferential surface. The bore in the cylindrical member is dimensioned such as to receive a needle-less syringe with the inlet/outlet orifice of the syringe in a fluid communicating relationship with the internal bore of the plunger. The plunger is axially moveable in response to insertion of the syringe into the internal bore of the cylindrical member and engagement with the plunger. The plunger moves from a first position in which the passageway of the cylindrical member and the passageway of the plunger are not in a fluid communicating relationship to a second position in which such passageways are in a fluid communicating relationship. This enables fluid to be transferred between the syringe orifice and the passageway of the cylindrical member.

In operation, the universal medication port may be inserted into a vial or the like with the passageway of the cylindrical member exposed to a fluid in the vial. Accordingly, when a syringe is inserted into the universal medication port, i.e., into the internal bore of the cylindrical member, the plunger will move to align the respective passageways of the plunger and the cylindrical member so that a fluid communicating relationship is established between the passageway of the cylindrical member and the orifice of the syringe. Consequently, when the plunger of the syringe is actuated, fluid will be withdrawn from the vial into the syringe without the use of any hypodermic needle. Thereafter, the fluid, thus withdrawn, may be introduced into an intravenous bottle or tubing having a universal medication port previously inserted therein. This is done by inserting the syringe into the universal medication port to align the respective passageways of the plunger and the cylindrical member. Then, when the plunger of the syringe is depressed, the fluid therein will be injected into the intravenous system, again without the use of any hypodermic needle.

Advantageously, a plurality of radial passageways are provided in both the plunger and the cylindrical member to enhance the withdrawal or delivery of fluid. Additionally, means are provided to assure alignment of the respective passages with each other upon insertion of a syringe.

Other features and advantages of the present invention will become apparent from the following description of the invention which refers to the accompanying drawings.

BRIEF DESCRIPTION OF THE DRAWINGS

FIG. 1 is an exploded view of a universal medication port embodying certain principles of the invention;

FIG. 2 is a cross-sectional view of the universal medication port of FIG. 1 in a closed or nonfluid communicating condition;

FIG. 3 is a cross-sectional view of the universal medication port in an open or fluid communicating condition;

FIG. 4 illustrates the use of the universal medication port to withdraw fluid from a vial or intravenous bottle; and FIG. 5 illustrates the use of universal medication ports in an intravenous delivery system.

DESCRIPTION OF A PREFERRED EMBODIMENT

Referring now to FIG. 1 of the drawings, there is shown an exploded view of a universal medication port 10 in accordance with the present invention. The universal medication port 10 comprises a top cap 11, a cylindrical member 12, a plunger 13, a spring 14 and a bottom cap 16.

The cylindrical member 12 includes an outer circumferential surface 17 and an inner bore 18 extending from one end 19 of the cylinder to the opposite end 21. The diameter of the bore 18 approximates the diameter of the plunger 13 so that the plunger 13 is received within the bore 18 in a close, but sliding, relationship. The bore 18 is reduced in diameter adjacent the end 19 to define a reduced section 22 and an internal shoulder 23 against which the plunger abuts. The diameter of the reduced section 22 is sized so as to receive, as seen in FIG. 2, the projecting end 24 of a syringe 26 to which a needle would normally be attached. The end face 19 has an external screw thread 27 which mates with internal threads (not shown) in the cap 11 or with internal screw threads (not shown) in the hypodermic syringe 26. The cylindrical member 12 also includes a plurality of radial fluid passageways, four such 28a, 28b, 28c and 28d, in the embodiment shown in FIG. 1, spaced 90° apart. Adjacent the end 21 of the cylindrical member 12, the cylinder has an external screw thread 29 for engagement with internal threads 31 in the bottom cap 16.

The function of the top cap 11 is to maintain the port 10 sterile when not in use. To this end, the cap 11 may include a short internal projecting member (not shown) which is inserted into the section 22 of the bore 18 when the cap is screwed onto the end 19 of the cylindrical member 12.

The plunger 13 includes a circumferential surface 32 and an internal bore 33. The internal bore 33 is sized so that it is equal to or greater than the inlet/outlet orifice 34 (FIG. 2) of the projecting end 24 of the syringe 26. The plunger 13 also includes a plurality of radial passageways 36a, 36b, 36c and 36d, equal in number to the passageways 28a, 28b, 28c and 28d in the cylinder 12 and generally of the same diameter and spacing, i.e., 90°. The plunger includes a pair of external longitudinal ribs 37 spaced 180° apart which mate with longitudinal grooves 38 in the internal surface 39 of the cylindrical member 12 which defines the internal bore 18. The ribs 37 and grooves 38 cooperate to angularly align the radial passageways 36a, 36b, 36c and 36d in the plunger 13 and the radial passageways 28a, 28b, 28c and 28d in the cylindrical member 12, and to prevent rotation of the members with respect to one another.

The plunger 13 is movable in response to screwing of the syringe 26 onto the end 19 of the cylindrical member 12 and consequent insertion of the projecting end 24 of the syringe 26 into the bore 18. The projecting end 24 of the syringe 26 engages the plunger 13 and moves it from the position shown in FIG. 2, in which the plunger abuts the shoulder 23 and the passageways 28a, 28b, 28c and 28d are not in a fluid communicating relationship with the corresponding passageways 36a, 36b, 36c and 36d ("closed position"), to the position shown in FIG. 3, in which the passageways 28a, 28b, 28c and 28d and the corresponding passageways 36a, 36b, 36c and 36d are aligned in fluid communicating relationships ("open position").

It should be appreciated that although the universal medication port 10 is illustrated as being used with a hypodermic syringe 26 of the type having a screw thread for mating with the screw thread of a hypodermic needle, the port 10 is not so limited and is equally usable with other types of hypodermic syringes not having screw threads. In such case, the projecting end of the syringe, rather than being inserted by screwing of the syringe onto the end 19, is directly inserted into the bore 18 by merely pushing it in.

The spring 14 serves to return the plunger 13 to its closed position upon removal of the syringe 26 from the port 10. The spring is housed in respective housings 41 and 42 in the cap 16 and in the plunger 13. The housings 41 and 42 are dimensioned such that the housing 41 nests within the housing 42.

FIGS. 4 and 5 illustrate examples of use of the universal port 10. All of the universal ports 10 employed in FIGS. 4 and 5 are identical, and each therefore is designated with the reference numeral 10. However, to differentiate the several ports, each will also be designated with a prime superscript, e.g., 10', 10", etc. The component parts of the ports 10 are not shown in FIGS. 4 and 5 and, accordingly, when referring to these parts, references will be made back to FIGS. 1-3 and unprimed references numerals used.

Referring now to FIG. 4, there is shown a vial or intravenous bottle 43 having a universal medication port 10' inserted in the neck 44 thereof. The action of the spring 14 (FIG. 2) maintains the port in its closed position, i.e., in a position in which the passageways 28a, 28b, 28c, and 28d of the cylindrical member 12 and the passageways 36a, 36b, 36c and 36d of the plunger 13 are not aligned in a fluid communicating relationship. To withdraw fluid from the vial 43, a syringe 46 is inserted into the port 10' to move the plunger 13 of the port 10' from its closed to its open position, whereby the passageways 28a, 28b, 28c and 28d and the corresponding passageways 36a, 36b, 36c and 36d are placed in a fluid communicating relationship. Thereafter the plunger 47 of the syringe 46 is actuated to withdraw fluid from the vial 43.

Referring now to FIG. 5, there is shown an intravenous delivery system comprising an intravenous bottle 48 having a pair of necks 49, 51. A standard connector 52 is inserted in the neck 49 and a length of tubing 53 having a branch connection 54 is connected to the connector 52. A universal port 10" is inserted into the neck 51 of the intravenous bottle 48 and a universal port 10''' is inserted into the branch 54. The ports 10" and 10''' are normally in a closed position. In operation, when it is desired to administer additional medication or fluid to the intravenous bottle 48, a syringe 56 is inserted into the port 10" to inject additional medication or fluid into the intravenous bottle. Additional medication or fluid may also be introduced directly into the tubing through the universal port 10''' by means of a syringe 57 inserted therein.

As should now be appreciated, the present invention provides a universal medication port which may be easily incorporated into a vial, intravenous bottle or intravenous tubing and which provides a simple, but effective, solution to eliminating the risk of healthcare workers being stuck by contaminated needles.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A universal medication port for use with a syringe having a body portion and a projection with an orifice for receiving and expressing a fluid, the port comprising:
    a cylindrical member having an outer circumferential surface, first and second opposed ends, and internal bore extending axially within the cylindrical member from the first end to the second end and at least one fluid passageway extending radially from the internal bore of the cylindrical member to the outer circumferential surface thereof;

a plunger disposed within the internal bore of the cylindrical member such as to be axially movable therein, the plunger having an outer circumferential surface, first and second opposite ends, an internal bore extending axially within the plunger from the first end toward the second end thereof and at least one passageway extending radially from the internal bore of the plunger to the outer circumferential surface thereof;

the bore in the cylindrical member being dimensioned so as to receive the projection of the syringe at the first end of the cylindrical member with the orifice thereof in a fluid communicating relationship with the internal bore of the plunger, and the cylindrical member being structured and arranged for engagement with the body portion of the syringe to releasably secure the body portion of the cylindrical member, the plunger being movable in response to insertion of the projection of the syringe into the internal bore of the cylindrical member and engagement of the projection with the plunger, the plunger being movable from a first position in which the passageway of the cylindrical member and the passageway of the plunger are not in a fluid communicating relationship to a second position in which such passageways are in a fluid communicating relationship, whereby fluid may be transferred between the orifice of the syringe and the passageway of the cylindrical member;

means for returning the plunger to the first position upon removal of the syringe from engagement with the plunger; and a first cap connected to the second end of the cylindrical member and wherein the returning means comprise a spring positioned intermediate the cap and the second end of the plunger.

2. The port of claim 1, further including means for angularly aligning the cylindrical member and the plunger to facilitate alignment of their respective fluid passageways into a fluid communicating relationship.

3. The port of claim 1, wherein the first cap is removably connected to the second end.

4. The port of claim 2 wherein the alignment means comprise at least one longitudinal rib on the circumferential surface of the plunger and a longitudinal groove in an internal surface of the cylindrical member for receiving the rib.

5. The port of claim 4, further including a second longitudinal rib on the circumferential surface of the plunger spaced 180 degrees from the one longitudinal rib and a second longitudinal groove in the internal surface of the cylindrical member spaced 180 degrees from the one longitudinal groove for receiving the second rib.

6. The port of claim 5 further including a second cap removably connected to the cylindrical member at the first end thereof.

7. A universal medication port for use with a syringe having an orifice for receiving and expressing a fluid, the port comprising:

a cylindrical member having an outer circumferential surface, first and second opposed ends, an internal bore defined by an inner surface of the cylindrical member extending axially within the cylindrical member from the first end to the second end, four fluid passageways spaced 90 degrees apart extending radially from the internal bore of the cylindrical member to the outer circumferential surface thereof and first and second longitudinal grooves spaced 180 degrees apart in the inner surface;

a plunger disposed within the internal bore of the cylindrical member such as to be axially movable therein, the plunger having an outer circumferential surface, first and second opposed ends, an internal bore extending axially within the plunger from the first end toward the second end thereof, four passageways extending radially from the internal bore of the plunger to the outer circumferential surface thereof, and first and second longitudinal ribs spaced 180 degrees apart on the outer circumferential surface of the plunger, the first and second ribs being received respectively in the first and second grooves to angularly align the passageways in the plunger with corresponding passageways in the cylindrical member;

the bore in the cylindrical member being dimensioned so as to receive the syringe with the orifice thereof in a fluid communicating relationship with the internal bore of the plunger, the plunger being movable in response to insertion of the syringe into the internal bore of the cylindrical member and engagement of the syringe from a first position in which the passageways of the cylindrical member and the passageways of the plunger are not in fluid communicating relationships to a second position in which such the corresponding passageways of the cylindrical member and the plunger are in a fluid communicating relationships, thereby enabling fluid to be transferred between the orifice of the syringe and the passageways of the cylindrical member;

a first cap removably connected to the cylindrical member at the second end thereof;

a compression spring disposed intermediate the first cap and the second end of the plunger for returning the plunger to the first position upon removal of the syringe from engagement with the plunger; and a second cap removably connected to the cylindrical member at the first end thereof.

8. A universal medication port for use with a syringe having an orifice for receiving and expressing a fluid, the port comprising:

a cylindrical member having an outer circumferential surface, first and second opposed ends, an internal bore defined by an inner surface of the cylindrical member extending axially within the cylindrical member from the first end to the second end, four fluid passageways spaced 90 degrees apart extending radially from the internal bore of the cylindrical member to the outer circumferential surface thereof;

a plunger disposed within the internal bore of the cylindrical member such as to be axially movable therein, the plunger having an outer circumferential surface, first and second opposed ends, an internal bore extending axially within the plunger from the first end toward the second end thereof, four passageways extending radially from the internal bore of the plunger to the outer circumferential surface thereof;

means for angularly aligning the passageways in the plunger with corresponding passageways in the cylindrical member;

the bore in the cylindrical member being dinmensioned so as to receive the syringe with the orifice thereof in a fluid communicating relationship with the internal bore of the plunger, the plunger being movable in response to insertion of the syringe into the internal bore of the cylindrical member and engagement of the syringe from a first position in which the passageways of the cylindrical member and the passageways of the plunger are not in fluid communicating relationships to a second position in which such corresponding passageways of the cylindrical member and the plunger are in fluid communicating relationships, thereby enabling fluid to be transferred between the orifice of the syringe and the passageways of the cylindrical member; and means for returning the plunger to the first position upon removal of the syringe from engagement with the plunger.

9. The port of claim 8, further including a first cap removably connected to the second end of the cylindrical member and wherein the returning means comprise a spring positioned intermediate the cap and the second end of the plunger.

10. The port of claim 8, wherein the alignment means comprise at least one longitudinal rib of the circumferential surface of the plunger and a longitudinal groove in an internal surface of the cylindrical member for receiving the rib.

11. The port of claim 10, further including a second longitudinal rib on the circumferential surface of the plunger spaced 180 degrees from the one longitudinal rib and a second longitudinal groove in the internal surface of the cylindrical member spaced 180 degrees from the one longitudinal groove for receiving the second rib.

* * * * *